US00PP09435P

United States Patent [19]

Saville

[11] Patent Number: Plant 9,435

[45] Date of Patent: Jan. 23, 1996

[54] MINIATURE ROSE PLANT NAMED 'SAVADEN'

[75] Inventor: F. Harmon Saville, Rowley, Mass.

[73] Assignee: Nor'East Miniature Roses, Inc., Rowley, Mass.

[21] Appl. No.: 364,500

[22] Filed: Dec. 27, 1994

[51] Int. Cl.[6] ..... A01H 5/00

[52] U.S. Cl. ..... Plt./10.1

[58] Field of Search ..... Plt./7.1, 10.1

[56] References Cited

U.S. PATENT DOCUMENTS

P.P. 4,330 11/1978 Delbard ..... Plt./22

*Primary Examiner*—Howard J. Locker
*Attorney, Agent, or Firm*—Christie, Parker & Hale

[57] ABSTRACT

A new miniature rose with orange to orange red flowers of good form.

1 Drawing Sheet

SUMMARY OF THE INVETNION

The present invention relates to a new and distinct variety of rose plant of the miniature rose class, which was created by me by crossing as seed parent the variety known as 'Ginger Snap' (U.S. Plant Pat. No. 4,330) and as pollen parent the variety known as 'Klima'. The varietal denomination of this new rose is 'Savaden'.

Among the novel characteristics possessed by this new variety which distinguishes it from its parents and all other varieties of which I am aware is its unusual orange to orange red flowers of good form which open well.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Ginger Snap'.

i Pollen parent.—*Klima'*.

Class Miniature.

The following observations are made of specimens grown under glass in Essex County, Mass., during the month of October.

FLOWER

Blooming habit: Recurrent.

A. Bud:

(1) *Size.*—Medium.

(2) *Form.*—Pointed, ovate.

(3) *Color.*—As sepals divide, bud color is near 42A.

(4) *Sepals.*—Slightly longer than bud, slight foliation.

(5) *Peduncle.*—Length — about 1¼ inch. Aspect — straight. Strength — erect. Color — near 144B.

B. Bloom:

(1) *Size.*—Average size when fully expanded — about 2 inches.

(2) *Borne.*—Singly.

(3) *Form.*—Cupped at first becoming flat, petals remaining loosely rolled under.

(4) *Petalage.*—Number of petals under normal conditions — about 21–27.

(5) *Color.*—During first two days, inner petals at center of flower near 25A; outer petals near 26A to 32A (outermost row); base of petals at point of attachment near 6A; reverse of petals near 45C and general tonality from an orange blend with orange red reverse. As bloom ages the general tonality gets lighter to near 29B with near 48C reverse.

C. Petals:

(1) *Texture.*—Thick, firm.

(2) *Appearance.*—Inside velvety and outside satiny.

(3) *Form.*—Wide, broad, ovate, fan shaped.

(4) *Arrangement.*—Imbricated, regularly arranged, shingle-like.

(5) *Petaloids in center.*—Few.

(6) *Persistence*—Persist.

(7) *Fragrance.*—Slight.

(8) *Lasting quality*—Very long on plant.

REPRODUCTIVE ORGANS

A. Stamens, filaments and anthers:

*Arrangement and color.*—Regularly arranged around styles. Color — near 23B.

B. Pollen:

*Color.*—Near 23A.

C. Styles: Medium length, even.

D. Stigmas:

*Color*—Near 18B.

E. Hips: None observed.

PLANT

A. Form: Upright.

B. Growth: Vigorous.

Height attained—About 16 to 20 inches.

C. Foliage: Compound 5 to 7 leaflets.

(1) *Size.*—Medium.

(2) *Quantity.*—Abundant.

(3) *Color.*—New foliage: Upper side — near 146A; Underside — near 146C. Old foliage: Upper side — near 147A; Underside — near 147C.

(4) *Shape.*—Oval, pointed.

(5) *Texture.*—Upper side is semi-glossy; underside is matte.

(6) *Edge.*—Serrated.

(7) Serration.—Serrate.

(8) *Leaf stem.*—Color — near 185A. Underside — 195A.

(9) Stipules—Medium, smooth.

(10) *Resistance to disease.*—Blackspot — average; Mildew — average; Rust — average.

D. Wood:

(1) *New wood.*—Color — near 146C; Bark — smooth.

(2) *Old wood.*—Color — near 146B; Bark — smooth.

E. Thorns:

(1) *Thorns.*—Quantity (main stalk) — average; On laterals from stalk — average; Form — straight, angled slightly downward; Length — medium; Color — near 184C; Position — irregular.

(2) *Prickles.*—None.

F. Winter hardiness: Needs protection in severe climates.

I claim:

1. A new and distinct variety of rose plant of the miniature rose class, substantially as shown and described.

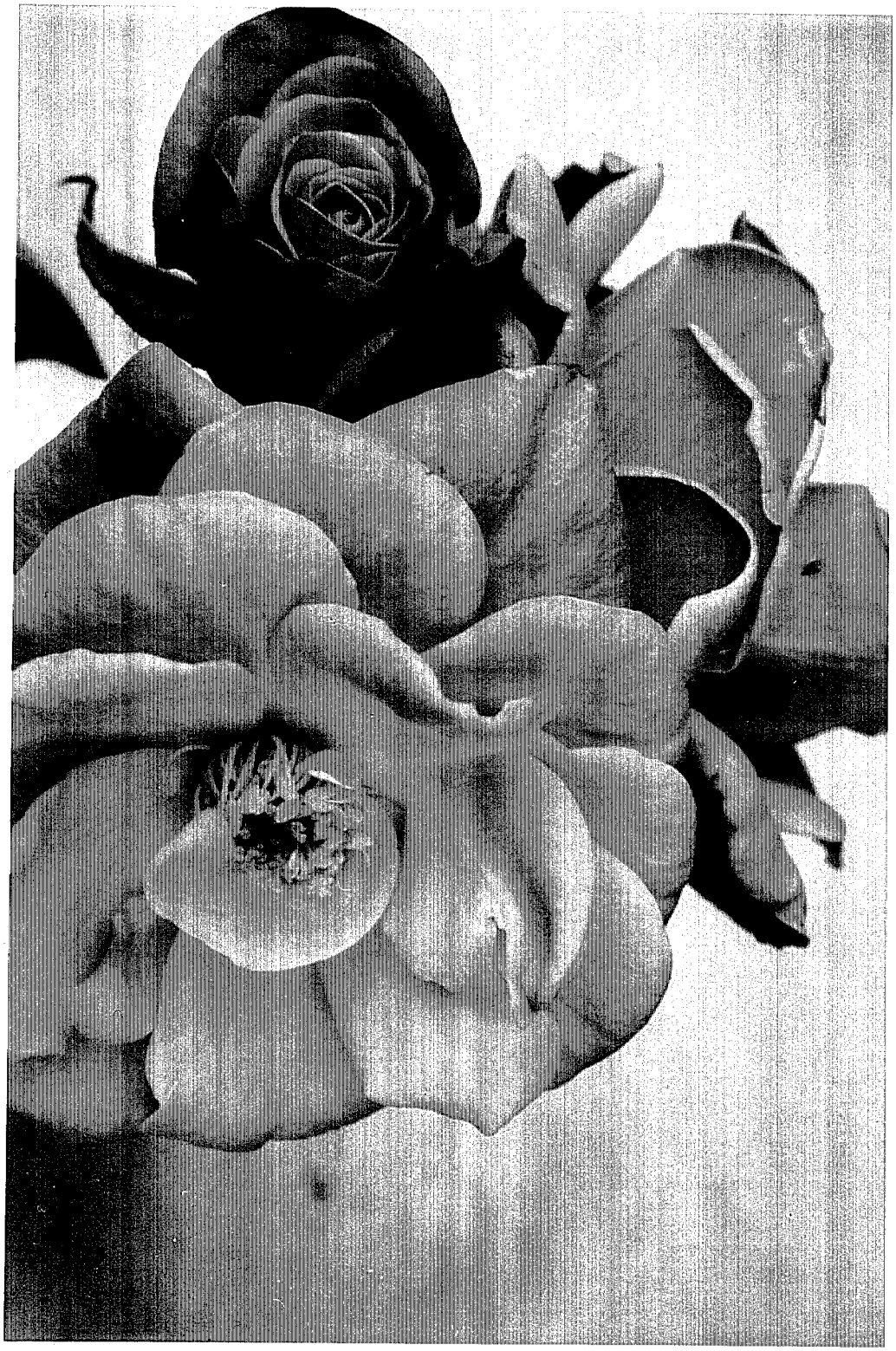

* * * * *